United States Patent
Christensen et al.

(10) Patent No.: US 6,828,137 B2
(45) Date of Patent: Dec. 7, 2004

(54) **METHODS FOR PRODUCING POLYPEPTIDES IN *ASPERGILLUS* MUTANT CELLS**

(75) Inventors: Bjorn Eggert Christensen, Bagsvaerd (DK); Henrik Mollgaard, Lyngby (DK); Svend Kaasgaard, Soborg (DK); Jan Lehmbeck, Vekso (DK)

(73) Assignee: Novozymes A/S, Bagsvaerd (DK)

( * ) Notice: Subject to any disclaimer, the term of this patent is extended or adjusted under 35 U.S.C. 154(b) by 357 days.

(21) Appl. No.: 10/099,704

(22) Filed: Mar. 15, 2002

(65) Prior Publication Data

US 2002/0197682 A1 Dec. 26, 2002

Related U.S. Application Data (62) Division of application No. 09/472,364, filed on Dec. 23, 1999, now Pat. No. 6,383,781.
(60) Provisional application No. 60/117,396, filed on Jan. 27, 1999, and provisional application No. 60/139,593, filed on Jun. 17, 1999.

(30) Foreign Application Priority Data

Dec. 23, 1998 (DK) .......................................... 1998 01726
May 27, 1999 (DK) .......................................... 1999 00745

(51) Int. Cl.$^7$ ............................. C12N 9/88; C12N 1/20; C12N 15/00; C07H 21/04
(52) U.S. Cl. ................. 435/232; 435/252.3; 435/320.1; 536/23.2
(58) Field of Search ............................. 435/232, 252.3, 435/320.1; 536/23.2

(56) References Cited

U.S. PATENT DOCUMENTS 6,383,781 B1 * 5/2002 Christensen et al. ....... 435/69.1

FOREIGN PATENT DOCUMENTS

| SU | 1271068 | 1/1994 |
| WO | 95/15390 | 6/1995 |
| WO | 95/15391 | 6/1995 |

OTHER PUBLICATIONS

Abstract of Article: Tudzynski et al., Mol. Gen. Genet. vol. 261, pp. 133–141 (1999).

* cited by examiner

*Primary Examiner*—Tekchand Saidha
(74) *Attorney, Agent, or Firm*—Elias J. Lambiris (57) ABSTRACT

The present invention relates to methods for producing a polypeptide of interest by (a) cultivating a mutant of a parent *Aspergillus* cell, wherein (i) the mutant comprises a first nucleic acid sequence encoding the polypeptide and a second nucleic acid sequence comprising a modification of at least one of the genes responsible for the biosynthesis or secretion of at least one toxin, and (ii) the mutant produces less of the toxin than the parent *Aspergillus* cell when cultured under the same conditions; and (b) isolating the polypeptide from the culture medium. Also, mutants of *Aspergillus* cells are provided, as well as methods for obtaining the mutant cells.

12 Claims, 2 Drawing Sheets

METHODS FOR PRODUCING POLYPEPTIDES IN ASPERGILLUS MUTANT CELLS

CROSS-REFERENCE TO RELATED APPLICATIONS

This application is a division of U.S. application Ser. No. 09/472,364 filed Dec. 23, 1999 now U.S. Pat. No. 6,383,781 and claims, under 35 U.S.C. 119, priority of Danish application nos. PA 1998 01726 filed Dec. 23, 1998, and PA 1999 00745 filed May 27, 1999 and U.S. provisional application No. 60/117,396 filed Jan. 27, 1999 and No. 60/139,593 filed Jun. 17, 1999, the contents of which are fully incorporated herein by reference.

FIELD OF THE INVENTION

The present invention relates to methods for producing polypeptides of interest in toxin-deficient *Aspergillus* mutant cells. The present invention also relates to mutants of *Aspergillus* cells and to methods for obtaining said mutant cells.

BACKGROUND OF THE INVENTION

The use of recombinant host cells in the expression of heterologous polypeptides has in recent years greatly simplified the production of large quantities of commercially valuable polypeptides, such as industrially important enzymes and secondary metabolites, which otherwise are obtainable only at lower quantities or by purification from their native sources. Currently, there is a varied selection of expression systems from which to choose for the production of any given polypeptide, including eubacterial and eukaryotic hosts. The selection of an appropriate expression system often depends not only on the ability of the host cell to produce adequate yields of the polypeptide with the desired composition and conformation, but, to a large extent, may also be governed by the intended end use of the protein.

One problem encountered in connection with the use of certain host systems is the production of mycotoxins. A number of fungi, which are used as host cells in the production of polypeptides of interest possesses genes encoding enzymes involved in the biosynthesis of various toxins. For example, cyclopiazonic acid, kojic acid, 3-nitropropionic acid and aflatoxins are known toxins, which are formed in, e.g., *Aspergillus flavus*. Similarly, trichothecenes are formed in a number of fungi, e.g., in *Fusarium* sp. such as *Fusarium venenatum* and in *Trichoderma*. A detailed overview of the formation of toxins in different fungi can be found in Handbook of Toxic Fungal Metabolites, Richard J Cole and Richard H. Cox, Academic Press, 1981.

The formation of such toxins during the fermentation of the polypeptides of interest is highly undesirable as they may present a health hazard to both operators, customers and the environment.

Consequently, a lot of effort is spent ensuring that such toxins are not formed under the conditions used in the relevant productions in levels considered to affect the health. This is mainly done by an extensive analytical program where the toxins are analyzed directly and by bioassays and/or feeding studies. In many cases these extensive programs are carried out on every single production batch affecting both production costs and the time before the products can be sold.

Cyclopiazonic acid (hereinafter also referred to as "CPA") is a weak acid ($pK_a$: 3.5) and precipitates under acidic conditions. It forms metal chelates, which can be split by dilute acid. It is quite toxic leading among other things to degenerative changes and necrosis in many organs, and selectively inhibits $Ca^{2+}$-ATPase. CPA is produced in an alpha- and beta-form, the beta-form being a precursor for the alpha-form. CPA is produced by Aspergilli but also by other fungi, such as *Penicilli*.

Kojic acid (hereinafter also referred to as "KA") is produced by a large number of *Aspergilli* but also by other fungi, such as *Penicilli*, and even by some bacteria. It is weakly alkaline ($pK_a$: 7.9; phenolic group), and forms complexes with many metal ions. It has antimicrobial activity and is weakly toxic to animals. It is a precursor for a number of synthetic compounds like insecticides, dyes, etc.

3-Nitropropionic acid (hereinafter also referred to as "3-NPA") is a natural nitro compound. It is produced by some fungi, especially *Aspergilli* (*A. flavus, A. wentii*) and *Penicilli* (*P. atroventum*). It has been reported in a few bacteria. The acid or its esters are also found in some plants. It is rather toxic in itself leading to, e.g., anemia. Also, it may be partly converted to another toxic compound nitrite in the gastrointestinal tract. 3-Nitropropionic acid affects Krebs cycle by inhibiting succinate dehydrogenase irreversibly and isocitrate lyase, fumarase and aspartase reversibly.

Aflatoxins are extremely biologically active, secondary metabolites produced by the fungi *Aspergillus flavus* Link ex. Fries and *Aspergillus parasiticus* Speare; see R. W. Detroy et al. "Aflatoxin and related compounds", In Microbial Toxins, Vol. 6 (A. Ciegler, S. Kadis, and S. J. Ajl, Eds.), Academic, New York, 1971, pp. 3–178. The major aflatoxins are $B_1$, $B_2$, $G_1$, and $G_2$. The metabolites, particularly aflatoxin $B_1$, are not only toxic to animals as well as humans but are also the most carcinogenic of all known natural compounds.

Malformins and ochratoxins are produced by *A. niger*.

By eliminating or reducing the ability of the host organisms to produce toxins both the regulatory approval procedure will be much simpler and time and money can be saved in the production phase as the analytical program can be reduced.

Currently, there is a need for toxin-deficient *Aspergillus* mutant cells (i.e., safe organisms preferably classified as GRAS), which are suitable for producing polypeptides of interest in an efficient and economical way. The present invention satisfies this need by providing the production of polypeptides of interest using toxin-deficient *Aspergillus* mutant host cells and by providing a method to construct such mutant host cells. There is also a need for providing *Aspergillus* mutant cells, which in parent form harbor (a) toxin gene(s), which is(are) not expressed, i.e., silent gene (s).

SUMMARY OF THE INVENTION

In accordance with one aspect of the present invention a method is provided for producing a polypeptide of interest by an *Aspergillus* mutant host cell, which comprises (a) cultivating a mutant of a parent *Aspergillus* cell, wherein (i) the mutant comprises a first nucleic acid sequence encoding the polypeptide and a second nucleic acid sequence comprising a modification of at least one of the genes responsible for the biosynthesis or secretion of at least one toxin, and (ii) the mutant produces less of the toxin than the parent *Aspergillus* cell when cultured under the same conditions; and (b) isolating the polypeptide from the culture medium.

In a preferred embodiment of the invention, the mutant *Aspergillus* cells produce at least about 90% less of the toxin than the parent cell when cultured under the same conditions. Preferably, the mutant produces less of a one or more of cyclopiazonic acid, kojic acid, 3-nitropropionic acid and aflatoxin than the parent *Aspergillus* cell when cultured under the same conditions.

According to another embodiment of the present invention toxin-deficient *Aspergillus* mutant host cells are provided useful for the production of a heterologous polypeptide of interest, which cell has been genetically modified in order to produce less of at least one toxin as compared to an *Aspergillus* parental cell, when cultured under the same conditions.

The *Aspergillus* mutant cells according to the invention are preferably selected from the group of *A. oryzae, A. aculeatus, A. nidulans, A. ficuum, A. flavus, A. foetidus, A. soja, A. sake, A. niger, A. japonicus, A. parasiticus*, and *A. phoenicus*.

In a further embodiment of the present invention a method is provided for obtaining a toxin-deficient *Aspergillus* mutant host cell, which comprises (a) introducing into an *Aspergillus* parent host cell a first nucleic acid sequence encoding a polypeptide of interest and a second nucleic acid sequence comprising a modification of at least one of the genes responsible for the biosynthesis or secretion of at least one toxin; and (b) identifying the mutant from step (a) comprising the nucleic acid sequences.

In an aspect the invention relates to *Aspergillus* mutant cells, suitable for the expression of heterologous polypeptides, wherein one or more silent toxin genes have been eliminate.

These and other embodiments will be outlined in further detail in the description, which will follow hereinafter.

DETAILED DESCRIPTION OF THE INVENTION

Definitions

For the purpose of the present application, the following terms are defined for a better understanding of the invention.

The term "vector(s)" means plasmid, cosmid, phage or any other vehicle to allow insertion, propagation and expression of a gene or DNA sequence encoding a polypeptide of interest including precursor forms thereof.

The term "host(s)" means any cell that will allow expression of a polypeptide of interest including precursor forms thereof.

The term "transformation" means incorporation permitting expression of heterologous DNA sequences by a cell.

The term "mutant" host (or strain) means a genetically modified strain, which includes both transformants and mutants of a wild type strain.

The term "toxin" means a metabolite of fungi with phytotoxic, zootoxic and antibiotic activity. The term "mycotoxin" is normally defined as a secondary metabolite produced by a fungus with the potential to cause an adverse health effect in humans and animals at levels of exposure. In the present context the terms "toxin" and "mycotoxin" may be used interchangeably.

The term "toxin deficient" as used about a mutant cell of the invention means that the mutant has an incomplete toxin production as compared to its parent strain, i.e., that the mutant produces less of at least one and preferably more than one toxins than the parent cell.

The term "same conditions" as used in step a) of the method of the invention relates the toxin production of the mutant to that of the parent cell and is intended to indicate that similar conditions, e.g., with respect to pH, temperature, oxygen, etc. are used for the fermentation of the mutant and the parent strain. The parent and mutant cells may be compared with regard to production of the toxin(s) in question under conditions conducive for the production of a polypeptide of interest or under conditions conducive for the production of the toxin(s).

Host Cells

The present invention provides mutants of *Aspergillus* host cells useful for the expression of polypeptides of interest, wherein the cells have been genetically modified in order to express significantly reduced levels of one or more toxins in comparison to a parental cell. The host cell is derived from the parental cell, which may be a wild type cell.

The host strains may be any *Aspergillus* host cell conventionally used for the expression of polypeptides of interest.

In a preferred embodiment, the *Aspergillus* host cell useful for the production of a polypeptide of interest is selected from the group consisting of the *Aspergillus* subgroups Eurotium (e.g., represented by the species *A. restrictus*), Chaetosartorya (e.g., represented by the species *A. cremeus*), Sclerocleista (e.g., represented by the species *A. ornati*), Satoia (e.g., represented by the species *A. niger*), Neosartorya (e.g., represented by the species *A. fumigatus, A. cervinus*), Hemicarpenteles (e.g., represented by the species *A. clavatus*), Petromyces (e.g., represented by the species *A. flavus, A. candidus, A. sparsus*), Emericella (e.g., represented by the species *A. nidulans, A. versicolor, A. ustus*), and Fenellia (e.g., represented by the species *A. terreus*).

In a particular preferred embodiment, the Aspergillus host cell is selected from the group consisting of *A. oryzae, A. aculeatus, A. ficuum, A. flavus, A. foetidus, A. soja, A. sake, A. niger, A. nidulans* and *A. japonicus*. Of these, *Aspergillus oryzae* and *Aspergillus niger, A. parasiticus*, and *A. phoenicus* are most preferred.

The above examples of host cells of the invention are named according to the presently accepted taxonomy.

Toxins

The toxin the production of which is to be reduced or eliminated according to the present invention may be any toxin produced by *Aspergilli* or encoded by a gene harbored in *Aspergilli*, but not necessarily expressed. For instance, it is know that aflatoxin genes are present in *A. oryzae*, but not expressed from this species. However, it may still be advantageous to eliminate aflatoxin pathway genes even though they are not expressed. This will be described further below and illustrated in Example 6.

In particular, the toxin to be reduced or eliminated is selected from the group consisting of cyclopiazonic acids (CPA), e.g., the alpha or beta form thereof, kojic acid (KA), 3-nitropropionic acid (NPA), emodin, malformins (e.g., Malformin A or B), aflatoxins, ochratoxins, flaviolin, and secalonic acids (e.g., secalonic D). For a further description of these toxins see the Background of the Invention section herein as well as the Handbook of Toxic Fungal Metabolites referred to in the section.

Dimethylallyl-cyclo-acetoacetyl-L-tryptophan Synthase (DCAT-S) of the Invention

The present invention also relates to isolated dimethylallyl-cycloacetoacetyl-L-tryptophan synthases obtained from a filamentous fungus, selected from the group consisting of (a) a dimethylallyl-cycloacetoacetyl-L-tryptophan synthase having the amino acid sequence of SEQ ID NO: 2; (b) an allelic variant of (a); and (c) a fragment of (a) or (b), wherein the fragment has dimethylallyl-cycloacetoacetyl-L-tryptophan synthase activity.

Preferably, the dimethylallyl-cycloacetoacetyl-L-tryptophan synthases of the present invention comprise the amino acid sequence of SEQ ID NO: 2, or an allelic variant thereof. In a more preferred embodiment, the dimethylallyl-cycloacetoacetyl-L-tryptophan synthases of the present invention comprise the amino acid sequence of SEQ ID NO: 2. In another preferred embodiment, a dimethylallyl-cycloacetoacetyl-L-tryptophan synthase of the present invention has the amino acid sequence of SEQ ID NO: 2 or fragments thereof, wherein the fragment has dimethylallyl-cycloacetoacetyl-L-tryptophan synthase activity. A fragment of SEQ ID NO: 2 is a polypeptide having one or more amino acids deleted from the amino and/or carboxy terminus of this amino acid sequence. In a most preferred embodiment, the dimethylallyl-cycloacetoacetyl-L-tryptophan synthase has the amino acid sequence of SEQ ID NO: 2.

Preferably, a fragment of SEQ ID NO: 2 has at least 320 amino avid residues, and most preferably at least 350 amino acid residues.

An allelic variant denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant of a polypeptide is a polypeptide encoded by an allelic variant of a gene.

The amino acid sequence of SEQ ID NO: 2 or a partial sequence thereof may be used to design an oligonucleotide probe, or a nucleic acid sequence encoding a dimethylallyl-cycloacetoacetyl-L-tryptophan synthase of the present invention, such as the nucleic acid sequence of SEQ ID NO: 1, or a subsequence thereof, may be used to identify and clone DNA encoding dimethylallyl-cycloacetoacetyl-L-tryptophan synthases from other filamentous fungal strains according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin).

Hybridization indicates that the nucleic acid sequence hybridizes to the oligonucleotide probe corresponding to the polypeptide encoding part of the nucleic acid sequence shown in SEQ ID NO: 1 or contained in pJaL499, under low to high stringency conditions (i.e., prehybridization and hybridization at 42° C. in 5×SSPE, 0.3% SDS, 200 micrograms/ml sheared and denatured salmon sperm DNA, and either 25, 35 or 50% formamide for low, medium and high stringencies, respectively), following standard Southern blotting procedures.

Thus, a genomic, cDNA or combinatorial chemical library prepared from other filamentous fungal strains may be screened for DNA which hybridizes with the probes described above and which encodes a dimethylallyl-cycloacetoacetyl-L-tryptophan synthase. Genomic or other DNA from other filamentous fungal strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, the carrier material is used in a Southern blot in which the carrier material is finally washed three times for 30 minutes each using 2×SSC, 0.2% SDS preferably at least 50° C., more preferably at least 55° C., more preferably at least 60° C., more preferably at least 65° C., even more preferably at least 70° C., and most preferably at least 75° C. Molecules to which the oligonucleotide probe hybridizes under these conditions are detected using X-ray film.

In a preferred embodiment, a dimethylallyl-cycloacetoacetyl-L-tryptophan synthase of the present invention is obtained from a strain of *Aspergillus*, and more preferably from *A. oryzae*, e.g., the polypeptide with the amino acid sequence of SEQ ID NO: 2.

As defined herein, an "isolated" dimethylallyl-cycloacetoacetyl-L-tryptophan synthase is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The present invention also relates to isolated nucleic acid sequences encoding dimethylallyl-cycloacetoacetyl-L-tryptophan synthases obtained from a filamentous fungus, and in a more preferred embodiment, the nucleic acid sequence is obtained from an *Aspergillus* sp, e.g., *A. oryzae*, in particular the nucleic acid sequence set forth in SEQ ID NO: 1. In another more preferred embodiment, the nucleic acid sequence is the sequence contained in plasmid pJaL499. The present invention also encompasses nucleic acid sequences which differ from SEQ ID NO: 1 by virtue of the degeneracy of the genetic code. The present invention also relates to subsequences of SEQ ID NO: 1 or the polypeptide encoding part of pJaL499, which encode polypeptide fragments which have dimethylallyl-cycloacetoacetyl-L-tryptophan synthase activity. A subsequence of SEQ ID NO: 1 or of the polypeptide encoding part of pJaL499 is a nucleic acid sequence encompassed by SEQ ID NO: 1 or the polypeptide encoding part of pJaL499 except that one or more nucleotides from the 5' and/or 3' end have been deleted. Preferably, a subsequence of SEQ ID NO: 1 contains at least 870 nucleotides, more preferably at least 960 nucleotides, and most preferably at least 1050 nucleotides.

The nucleic acid sequences may be obtained from microorganisms that are taxonomic equivalents of *Aspergillus oryzae*.

The techniques used to isolate or clone such nucleic acid sequences are described herein. The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. The nucleic acid sequence may be of genomic, cDNA, RNA, semi-synthetic, synthetic origin, or any combinations thereof.

Modification of a nucleic acid sequence encoding a dimethylallyl-cycloacetoacetyl-L-tryptophan synthase of the present invention may be necessary for the synthesis of enzymes substantially similar to the polypeptide. The term "substantially similar" to the dimethylallyl-cycloacetoacetyl-L-tryptophan synthase refers to non-naturally occurring forms of the enzyme. These dimethylallyl-cycloacetoacetyl-L-tryptophan synthases may differ in some engineered way from the enzyme isolated from its native source. For example, it may be of interest to synthesize variants of the enzyme where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO: 1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the polypeptide, or by introduction of nucleotide substitutions which may give rise to a different amino acid sequence. For a general description of nucleotide substitution, see, e.g., Ford et al., 1991, Protein Expression and Purification 2: 95–107.

It will be apparent to those skilled in the art that such substitutions can be made outside the regions critical to the function of the molecule and still result in a biologically active dimethylallyl-cycloacetoacetyl-L-tryptophan synthase. Amino acid residues essential to the activity of the dimethylallyl-cycloacetoacetyl-L-tryptophan synthase encoded by an isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244: 1081–1085). In the latter technique, mutations are introduced at every positively charged residue in the molecule, and the resultant mutant molecules are tested for dimethylallyl-cycloacetoacetyl-L-tryptophan synthase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306–312; Smith et al., 1992, Journal of Molecular Biology 224: 899–904; Wlodaver et al., 1992, FEBS Letters 309: 59–64).

A preferred use of the nucleic acid sequence of the invention or homologues or fragments thereof is to eliminate or reduce the dimethylallyl-cycloacetoacetyl-L-tryptophan synthase activity of a given host cell, in particular a cell of A. oryzae, thereby reducing or eliminating the production of CPA from said cell.

The present invention also relates to nucleic acid constructs, recombinant expression vectors, and host cells containing the nucleic acid sequence of SEQ ID NO: 1 or the polypeptide encoding part of pJaL499, subsequences or homologues thereof, for expression of the sequences. The constructs and vectors may be constructed as described herein. The host cell may be any cell suitable for the expression of the nucleic acid sequence and may be selected e.g., from the parent or mutant cells described herein.

Genetic Modifications of the Host Cell

In order to express significantly reduced levels of one or more toxins, the host cell of the invention is genetically modified which may be achieved by using standard technologies known to the person skilled in the art. The gene sequences responsible for production of toxin activity may be inactivated or partially or entirely eliminated. Thus, an *Aspergillus* mutant host cell according to the invention expresses reduced or undetectable levels of one or more toxins.

In a particular embodiment, the inactivation is obtained by modification of the respective structural or regulatory regions (such as genes) involved in the formation or secretion of the toxin of choice. Known and useful techniques include, but are not limited to, specific or random mutagenesis, PCR generated mutagenesis, site specific DNA deletion, insertion and/or substitution, gene disruption or gene replacement, anti-sense techniques, or a combination thereof.

Mutagenesis may be performed using a suitable physical or chemical mutagenizing agent. Examples of a physical or chemical mutagenezing agent suitable for the present purpose include, but are not limited to, UV irradiation, ionizing irradiation such as gamma irradiation, hydroxylamine, N-methyl-N'-nitro-N-nitrosoguanidine (MNNG), O-methyl hydroxylamine, nitrous acid, ethyl methane sulphonate (EMS), sodium bisulfite, and nucleotide analogues. When such agents are used the mutagenesis is typically performed by incubating the cell to be mutagenized in the presence of the mutagenizing agent of choice under suitable conditions, and selecting for cells showing a significantly reduced production of the targeted toxin(s).

Reduction or elimination of the production of a given toxin by a host cell may also be achieved by modification of a nucleotide sequence involved in or otherwise necessary for the production or secretion of the toxin. For instance, the nucleotide sequence may encode a gene product having a necessary function in the pathway leading to toxin production. Nucleotide sequence may, e.g., be the one shown in SEQ ID NO: 1 or the polypeptide encoding part of pJaL499. Modification may be accomplished by the introduction, substitution or removal of one or more nucleotides in the nucleotide sequence or a regulatory element required for the transcription or translation of the sequence. For example, nucleotides may be inserted or removed so as to result in the introduction of a stop codon, the removal of a start codon or a change of the open reading frame of the nucleotide sequence. The modification or inactivation of the sequence or a regulatory element thereof may be accomplished by site-directed or random mutagenesis or PCR generated mutagenesis in accordance with methods known in the art. Although, in principle, the modification may be performed in vivo, i.e., directly on the cell expressing the toxin gene(s), it is presently preferred that the modification be performed in vitro as exemplified below.

An example of a convenient way to inactivate or reduce production of a toxin of interest, e.g., CPA, of a filamentous fungal cell of choice is based on techniques of gene replacement, gene deletion, or gene disruption. For example, in the gene disruption method, a nucleic acid sequence corresponding to the endogenous gene or gene fragment of interest (e.g., the DCAT-S gene of the invention) is mutagenized in vitro to produce a defective nucleic acid sequence which is then transformed into the parent cell to produce a defective gene. By homologous recombination, the defective nucleic acid sequence replaces the endogenous gene or gene fragment. It may be desirable that the defective gene or gene fragment also encodes a marker, which may be used for selection of transformants in which the nucleic acid sequence has been modified or destroyed.

Alternatively, modification or inactivation of the gene may be performed by established anti-sense techniques using a nucleotide sequence complementary to the nucleic acid sequence of the gene. More specifically, expression of the gene by a filamentous fungal cell may be reduced or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

Following mutagenesis or other modification of genes of a toxin pathway the mutants are screened for reduced or eliminated toxin production. Specific examples of how to screen for toxins are given in the examples below. Alternatively, useful screening assays are described in the "Handbook of Toxic Fungal Metabolites" or are available at institutions normally checking the level of mycotoxins in, e.g., foodstuffs.

Therefore, due to genetic modification, the *Aspergillus* mutant host cell according to the present invention expresses significantly reduced levels of toxin(s). In a preferred embodiment, the level of these toxin(s) expressed by the mutant host cell has been reduced individually more than about 50%, preferably more than about 85%, more preferably more than about 90%, and most preferably more than about 95%, or even more than 99%. In another preferred embodiment these toxins in the mutant host cell according to the invention may be reduced in any combination. In a further preferred embodiment, the product expressed by the host cell is essentially free from at least one toxin of the group of cyclopiazonic acid, kojic acid, 3-nitropropionic acid, emodin, malformin, aflatoxins, ochratoxins and secalonic acids. In particularly preferred embodiment, the product expressed by the host cell is essentially free from at least cyclopiazonic acid, more particularly free from at least cyclopiazonic acid and kojic acid or an aflatoxin, and most preferably free from at least cyclopiazonic acid, kojic acid and 3-nitropropionic acid.

In a preferred embodiment the host cell is a strain of *A. oryzae* having a reduced or eliminated production of one or more of NPA, CPA, kojic acid (KA) or maltoryzin, preferably at least two of these toxins such as NPA and CPA; NPA and KA; CPA and KA; or NPA, CPA and KA. Furthermore, in addition to the elimination or reduction of one or more of these toxins, preferably a gene of an aflatoxin pathway of choice is inactivated so that the resulting mutant strain is unable to produce the aflatoxin. Aflatoxin genes from *A. flavus* are well known and may be used to identify the corresponding genes in *A. oryzae*, which can then be inactivated by methods known in the art.

In another preferred embodiment the host cell is a strain of *A. niger* or *A. ficuum* having a reduced or eliminated production of one or more of malformin (eg malformin A1 or B), an ochratoxin (e.g., ochratoxin A), and flaviolin, preferably at least two of these toxins such as malformin and ochratoxin; malformin and flaviolin; ochratoxin and flaviolin; and malformin, ochratoxin and flaviolin.

In another preferred embodiment the host cell is a strain of *A. aculeatus* having a reduced or eliminated production of one or more of one of the secalonic acids (e.g., secalconic acid D) or emodin (a precursor to secalonic D), preferably of both of these types of toxin.

Methods of Producing Polypeptides

By the method of the present invention, the amount of certain targeted toxin(s) is significantly reduced, whereas the characteristics of the mutant host cell in terms of stable maintenance in the cell of the genetically modified genes encoding the polypeptide of interest, production capability of the cell and yield of the polypeptide of interest is substantially maintained. More specifically, by the method of the invention, the host cell is genetically modified within structural and/or regulatory regions necessary for the production or secretion of one or more toxins of interest thereby eliminating or reducing the production or secretion of said toxin(s).

Therefore, another aspect of the invention provides a method of producing polypeptides or proteins in an *Aspergillus* mutant host cell according to the invention, including heterologous polypeptides or proteins, which method comprises introducing into said mutant host cell a nucleic acid sequence encoding the polypeptide of interest, cultivating the mutant host cell in a suitable growth medium, and recovering said polypeptide of interest.

Thus, the mutant host cell according to the invention must contain structural and regulatory genetic regions necessary for the expression of the polypeptide of interest. The nature of such structural and regulatory regions depends to a large extent on the product aimed and the particular *Aspergillus* host strain. The genetic design of the host cell according to the invention may be accomplished by the person skilled in the art using standard recombinant DNA technology for the transformation or transfection of a host cell (see, e.g., Sambrook et al.).

Preferably, the host cell is modified by methods known in the art for the introduction of an appropriate cloning vehicle, i.e., a plasmid or a vector, comprising a DNA fragment encoding the desired polypeptide of interest. The cloning vehicle may be introduced into the host cell either as an autonomously replicating plasmid or integrated into the chromosome. Preferably, the cloning vehicle comprises one or more structural regions operably linked to one or more appropriate regulatory regions.

The structural regions are regions of nucleotide sequences encoding the polypeptide of interest. The regulatory regions include promoter regions comprising transcription and translation control sequences, terminator regions comprising stop signals, and polyadenylation regions. The promoter, i.e., a nucleotide sequence exhibiting a transcriptional activity in the host cell of choice, may be one derived from a gene encoding an extracellular or an intracellular protein, preferably an enzyme, such as an amylase, a glucoamylase, a protease, a lipase, a cellulase, a xylanase, an oxidoreductase, a pectinase, a cutinase, or a glycolytic enzyme. Examples of suitable promoters for directing the transcription of the nucleic acid constructs in the methods of the present invention are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Aspergillus oryzae* acetamidase (amdS), *Fusarium oxysporum* trypsin-like protease (U.S. Pat. No. 4,288,627), and mutant, truncated, and hybrid promoters thereof. Particularly preferred promoters are the NA2-tpi promoters (a hybrid of the promoters from the genes encoding *Aspergillus niger* neutral alpha-amylase and *Aspergillus oryzae* triose phosphate isomerase), glucoamylase, and TAKA amylase promoters.

The cloning vehicle may also include a selectable marker. A selectable marker is a gene the product of which provides for biocide or viral resistance, resistance to heavy metals, prototrophy to auxotrophs, and the like. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

Furthermore, selection may be accomplished by co-transformation, wherein the transformation is carried out with a mixture of two vectors and the selection is made for one vector only.

The procedures used to ligate the DNA construct of the invention, the promoter, terminator and other elements, respectively, and to insert them into suitable cloning vehicles containing the information necessary for replication, are well known to persons skilled in the art (see, e.g., Sambrook et al., 1989; ibid.).

The mutant filamentous fungal cell is cultivated in a nutrient medium suitable for production of a polypeptide of interest using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the heterologous polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium.

The polypeptide may be detected using methods known in the art that are specific for the polypeptide. These detection methods may include use of specific antibodies, formation of an enzyme product, disappearance of an enzyme substrate, or SDS-PAGE. For example, an enzyme assay may be used to determine the activity of the polypeptide. Procedures for determining enzyme activity are known in the art for many enzymes.

The resulting polypeptide may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989).

Products

The desired end product, i.e., the polypeptide of interest expressed by the *Aspergillus* mutant host cell, may be any homologous or heterologous protein or peptide.

The polypeptide may be any polypeptide heterologous to the mutant filamentous fungal cell. The term "polypeptide" is not meant herein to refer to a specific length of the encoded product and, therefore, encompasses peptides, oligopeptides, and proteins. The heterologous polypeptide may also be an engineered variant of a polypeptide. The term "heterologous polypeptide" is defined herein as a polypeptide, which is not native to the filamentous fungal cell. The mutant filamentous fungal cell may contain one or more copies of the nucleic acid sequence encoding the heterologous polypeptide.

In the methods of the present invention, the mutant filamentous fungal cell may also be used for the recombinant production of polypeptides, which are native to the cell. The native polypeptides may be recombinantly produced by, e.g., placing a gene encoding the polypeptide under the control of a different promoter to enhance expression of the polypeptide, to expedite export of a native polypeptide of interest outside the cell by use of a signal sequence, and to increase the copy number of a gene encoding the polypeptide normally produced by the cell. The present invention also encompasses, within the scope of the term "heterologous polypeptide", such recombinant production of homologous polypeptides, to the extent that such expression involves the use of genetic elements not native to the cell, or use of native elements which have been manipulated to function in a manner that do not normally occur in the host cell.

In a more specific embodiment, the product is a therapeutically active peptide or protein, such as a hormone, in particular insulin, growth hormone, glucagon, or somatostatin; an interleukin, in particular interferon; a haematopoietic growth factor, in particular PDGF (platelet derived growth factor), EPO (erythropoietin), or TPO (thrombopoietin); a protease, in particular factor VII, factor VIII, urokinase, chymosin, or TPA; or serum albumin.

In another preferred embodiment, the product is an enzyme of fungal or bacterial origin. The enzyme is preferably a glycosidase enzyme, e.g., an amylase, in particular an alpha-amylase, a beta-amylase or a glucoamylase; a glucan alpha-1,4-glucosidase; an aminopeptidase; a carbohydrase; a carboxypeptidase; a catalase; a cellulase, in particular an beta-1,4-endoglucanase or a beta-1,3(4)-endoglucanase; a cellulose-beta-1,4-cellobiosidase; a chitinase; a cutinase; a cyclodextrin glycosyltransferase; a deoxyribonuclease; a galactanase; a galactosidase, in particular an alpha-galactosidase or a beta-galactosidase; an endoglucanase, in particular an beta-1,3-endoglucanase, an alpha-1,3-endoglucanase, an beta-1,2-endoglucanase, or a beta-1,6-endoglucanase; a glucosidase, in particular an alpha-glucosidase or a beta-glucosidase; an invertase; a laccase; a lipolytic enzyme, in particular a lipase, an esterase, a phospholipase, or a lyso-phospholipase; a lyase or a pectate lyase; a mannase; a mannosidase; a polygalacturonase; a mutanase; an oxidase or an oxidoreductase, such as a peroxidase or a polyphenoloxidase; an oxygenase; a pectinase, an endo-peptidase or an exo-peptidase; a phytase; a polygalacturonase; a protease; a ribonuclease; a transglutaminase; and a xylanase, in particular a beta-1,4-endoxylanase or a xylan-beta-1,3-endoxylosidase.

In another preferred embodiment the product is a hybrid polypeptide, such as prochymosin and pro-trypsin-like proteases. The heterologous protein expressed by the host cell may, under suitable conditions, e.g., absence of substantial protease activities, also be a precursor protein such as a zymogen, a hybrid protein, a protein obtained as a pro sequence or a pre-pro sequence, or any other immature form.

The invention is further illustrated with reference to the following examples, which should not in any way be construed as limiting the scope of the invention as defined in the appended claims.

Aspergillus Mutants Having Silent Toxin Gene(s) Eliminated

The biosynthtic pathway for aflatoxin has been studied in the aflatoxinogenic species *Aspergillus flavus* and *Aspergillus parasiticus*. In both species a number of genes have been identified and shown to map in a large cluster (reviewed by Woloshuk, C. P. and Prieto, R, FEMS Microbiology Letter (1998) 160:169–176). Several of the genes, including aflR, which encodes a gene regulating expression of the other pathway genes, and omtA, encoding O-methyltransferase, have been cloned and sequenced.

Aflatoxin genes are present in the genome of *A. oryzae*, but are not expressed from this species. Even though no aflatoxin is expressed it is still advantageous to eliminate one or more of these silent aflatoxin pathway genes. *Aspergilli* mutants, e.g., *A. oryzae* mutants, having aflatoxin genes, such as the aflR and/or omtA genes, eliminated are advantageous, because then new mutant strains need not be tested for production of the aflatoxin(s) in question.

Thus, in an aspect the invention relates to *Aspergillus* mutant cells, suitable for the expression of heterologous polypeptides, wherein one or more silent toxin genes have been eliminate.

That the silent toxin gene(s) have been "eliminated" means that gene(s) in question have been changes or removed, e.g., by gene replacement or disruption techniques well known in the art (see, e.g., Miller et al., 1985, Molecular and Cellular Biology, p. 1714–1721), in a manner resulting in that said silent gene(s) is(are) not comprised in the mutant cell.

The term "silent" toxin gene(s) means that the toxin gene(s) are not expressed.

The toxin gene(s) may be eliminated by non-revertably detetion or disruption of all or part of the toxin gene(s).

The term "non-revertably deletion or disruption of all or part of the toxin gene(s)" means that the toxin gene(s) in question have been either removed or changed in a manner so that said genes do not encode a toxin and cannot naturally mutate back, e.g., during production to a was gene encoding a toxin.

*Aspergillus* cells in question are any of the above described and may be selected from the group consisting of the *Aspergillus* subgroups *Eurotium*, *Chaetosartorya*, *Sclerocleista*, *Satoia*, *Neosartorya*, *Hemicarpenteles*, *Petromyces*, *Emericella*, and *Fenellia*.

Toxin gene(s) in question encoding one or more toxins include toxins selected from the group consisting of cyclopiazonic acid, kojic acid, 3-nitropropionic acid, emodin, malformin, aflatoxins, ochratoxins and secalonic acids.

Specifically contemplated are toxin gene(s) encoding an aflatoxin, in particular toxin gene(s) from the *A. oryzae* aflatoxin cluster, in particular selected from the group comprising omtA, aflR, pksA, Nor-1, fas-beta, fas-alpha, vber-1, avnA, ord-2.

The parent *Aspergillus* cell may be an *A. oryzae* cell, in particular *A. oryzae* A1560 (IFO 0417).

Experimental
Materials and Methods
1. Strains

*Aspergillus oryzae* A1560 is equal to IFO 04177 (see below). *Aspergillus oryzae* IFO 4177: available from Institute for Fermentation, Osaka; 17–25 Juso Hammachi 2-Chome Yodogawaku, Osaka, Japan; see also WO 98/12300.

JaL228: *Aspergillus oryaze* strain in which the gene for a neutral metalloprotease, NpI, is disrupted; the construction of this strain is described in WO 98/12300.

BECh 1: The construction of this CPA negative *Aspergillus oryaze* strain is described in Example 1.

BECh 2: The construction of this CPA negative and KA negative *Aspergillus oryaze* strain is described in Example 1.

BECh 3: The construction of this CPA negative and KA negative *Aspergillus oryaze* strain is described in Example 1.

BZ14: A strain of *Aspergillus oryaze* A1560 cotransformed with ToC90 and phD450 as described in WO 92/17573.

JaL 250: The construction of this *Aspergillus oryaze* strain is described in Example 6.

Deposit

An *E. coli* strain containing the plasmid pJaL499 was deposited with DSMZ-Deutsche Sammlung von Mikroorganismen und Zellkulturen GmbH, Mascheroder Weg 1b, D-38124 Braunschweig on Jan. 13, 1999, and obtained the deposit number DSM 12622.

2. Genes

DMAT-S: This gene codes for dimethylallyl-L-tryptophan synthase, an enzyme involved in the biosynthesis of ergot alkaloid.

DCAT-S: This gene codes for dimethylallyl-cyclo-acetoacetyl-L-tryptophan synthase, an enzyme involved in the biosynthesis of cyclopiazonic acid (CPA).

pyrG: This gene codes for orotidine-5'-phosphate decarboxylase, an enzyme involved in the biosynthesis of uridine.

3. Plasmids pAHL: This plasmid is described in WO 97/07202.

pCaHj483: This plasmid is described in WO 98/00529.

pCaHj493: This plasmid is described in Example 2.

pJaL335: This plasmid is described in WO 98/12300.

pJaL499: This plasmid is described in Example 4.

4. Media and Solutions

Chemicals used as buffers and substrates were commercial products of at least reagent grade.

Screening Medium 1 (Per Liter)

| | |
|---|---|
| Mannitol | 30 g |
| Glucose | 10 g |
| Succinic acid | 10 g |
| Casamino acids | 3 g |
| KH$_2$PO$_4$ | 1 g |
| MgSO$_4$*7H$_2$O | 0.3 g |
| FeSO$_4$*7H$_2$O | 0.2 g |
| 2,6-dichloro-4-aniline | 2 ppm |
| agar | 20 g |

Final pH 5.6, adjusted with 14% NH$_4$OH.

Cove N

| | |
|---|---|
| Cove Salt solution | 50 ml |
| Sorbitol | 218 g |
| dextrose | 10 g |
| potassium nitrate | 2.02 g |
| Agar | 35 g |
| deionized water | 1000 ml |

COVE Salt Solution (Per Liter)

| | |
|---|---|
| KCl | 26 g |
| $MgSO_4$ | 26 g |
| $KH_2PO_4$ | 76 g |
| Trace Metals Sol'n | 50 ml |
| $CHCl_3$ | 2 ml |

Trace Metals Solution (Per 1 Liter)

| | |
|---|---|
| $Na_2B_4O_7*10H_2O$ | 40 mg |
| $CuSO_4*5H_2O$ | 400 mg |
| $FeSO_4*7H_2O$ | 800 mg |
| $MnSO_4*2H_2O$ | 800 mg |
| $Na_2MoO_4*2H_2O$ | 800 mg |
| $ZnSO_4*7H_2O$ | 8000 mg |

Gl-gly

| | |
|---|---|
| yeast extract | 18 g |
| Glycerol 87% | 24 ml |
| Pluronic PE6100 | 1 ml |
| Tap water ad | 1000 ml |

1/5 MDU-2BP

| | |
|---|---|
| maltose | 9 g |
| $MgSO_4*7H_2O$ | 0.2 g |
| NaCl | 0.2 g |
| $K_2SO_4$ | 0.4 g |
| $KH_2PO_4$ | 2.4 g |
| Yeast Extract | 1.4 g |
| AMG Trace Metals | 0.1 ml |
| Pluronic PE6100 | 0.02 ml |
| Deionized Water ad | 1000 ml |

Final pH 5.0; prior to inoculation, 1.0 ml of 50% urea is added.

MDU-IB (Per 1 Liter)

| | |
|---|---|
| Maltodextrin MD01 | 45.0 g |
| $MgSO_4*7H_2O$ | 1.0 g |
| NaCl | 1.0 g |
| $K_2SO_4$ | 2.0 g |
| $KH_2PO_4$ | 12.0 g |
| Yeast Extract | 7.0 g |
| AMG Trace Metals | 0.5 ml |
| Pluronic PE6100 | 1 ml |
| Final pH 5.0; | |

Prior to inoculation, 1,3 ml of 50% urea/100 ml medium is added.

AMG Trace Metals Solution (Per 1 Liter)

| | |
|---|---|
| $FeSO_4*7H_2O$ | 13.9 g |
| $MnSO_4*H_2O$ | 8.45 g |
| $ZnCl_2$ | 6.8 g |
| $CUSO_4*5H_2O$ | 2.5 g |
| $NiCl_2*6H_2O$ | 2.5 g |
| Citric acid | $\geq 3.0$ g |
| Trace Metal Solution | 1 ml |

KM2 Medium (Per 1 Liter)

| | |
|---|---|
| Yeast extract | 2.5 g |
| $K_2HPO_4$ | 10 g |
| $MgSO_4*7H_2O$ | 0.5 g |
| KCl | 0.5 g |
| $FeSO_4$ | 0.01 g |
| glucose | 100 g |
| Final pH adjusted to 6.0 | |

For use in solid plates, KMZ medium is solidified with agar, 20 g/l.

Triton X-100 at 300 µl/l is added as a colony growth restriction agent.

Nakamura Medium (Per 1 Liter)

| | |
|---|---|
| Sucrose | 50 g |
| Peptone | 20 g |
| $KH_2PO_4$ | 5 g |
| $CaHPO_4$ | 2.5 g |
| $MgSO_4$ | 2.5 g |
| Final pH is adjusted to 6.4 | |

5. Assays

A. Assay Procedure for CPA by HP Capillary Electrophoresis

One ml aliquot of sample is prepared for capillary electrophoresis (CE) analysis by solid phase extraction on a Supelclean LC-18 SPE tube (prepacked 3 ml column from Supelco, cat. no. 5-7012, conditioned with 2 ml methanol and 2 ml Milli-Q water). A suction manifold is used in order to force the fluids through the column. After washing with 3 ml Milli-Q water, the sample is eluted with 3 ml methanol. Without further treatment, eluate is then subjected to CE analysis. Occasionally a precipitate forms which is removed by centrifugation.

The CE analysis is performed using a Hewlet-Packard photo-diode array CE-apparatus (3D-CE). The sample is injected under hydrostatic pressure of 34 mbar over 10 sec. A 50 mm capillary (56 cm effective length) at 30° C. is used which has been conditioned with 0.1 M NaOH for 1 min, followed by 100 mM borate/NaOH pH 9.1 for 5 min. The voltage is set at 17 kV. UV-spectra are always collected to identify the peak, but the run is followed at 280 nm. A commercial cyclopiazonic acid is used as a standard (Sigma Co., St. Louis Mo., USA, catalog no. Cl530, minimum 98% pure). The lower limit of sensitivity of the method is approximately 1 ppm.

B. Assay Procedures for CPA by Thin Layer Chromatography (TLC)

1. Analysis of Plate Cultures

Agar plugs are analyzed as described in Filtenborg O., Frisvad J. C. and Svendsen J. A.: "Simple Screening Method for Mold Producing Intracellular Mycotoxins in Pure Cultures", Applied and Environmental Microbiology (1983) 45:581–585.

2. Analysis of Liquid Cultures

10 µl samples of supernatant are applied at both opposite edges of a TLC plate (Merck Silica Gel 60). Aliquots of cyclopiazonic acid, Sigma C 1530, dissolved and diluted in a mixture of methanol: chloroform (1:2 by volume) to 50 ppm, 25 ppm, 5 ppm and 2.5 ppm are used as standards. The plate is first developed in CAP (chloroform: acetone: propan-2-ol=85:15:20 by volume) for 15 minutes, allowed to dry, then turned around and the other half is subsequently developed in TEF (toluene: ethyl acetate: formic acid=5:4:1 by volume) for 15 minutes.

Alternatively the plate is developed in EMA (ethyl acetate: methanol: 25% ammonium hydroxide=16:8:2 by volume) and TEF each for 15 minutes as described above.

The plate is allowed to dry thoroughly (1 hour) in a fume hood, before spraying with Ehrlich reagent (2 g of 4-dimethylaminobenzaldehyde in 85 ml 96% ethanol to which 15 ml 37% hydrochloric acid is subsequently added).

CPA is seen as bluish-violet mushroom shaped spots with a typical low migration in the CAP system (a neutral system) whereas the acidic TEF system yields a typical prolonged smear midways between the application site and the front of developer. In the EMA system (basic/alkaline system) the cyclopiazonic acid is focused to small dense spots.

By direct visual inspection of the plates, CPA concentrations $\geq 2.5$ ppm can be seen as purple zones smears or spots (depending on the development system). By scanning the TLC plate on a desktop flatbed scanner and then processing and enhancing the electronic image in a suitable Image Processing Programme (in this case Paint Shop Pro 4) the sensitivity is improved with a factor 5 to 10.

The overall sensitivity of this analysis is (without extraction) approx. 0.5–1 ppm CPA; using extracts improves the sensitivity at least 10-fold.

C. Assay Procedure for Kojic Acid by Capillary Electrophoresis

An aliquot of 1 to 3 ml of sample is prepared for CE analysis by solid phase extraction on a Supelclean LC-18 SPE tube (prepacked 3 ml column from Supelco, cat. no. 5-7012), conditioned with methanol followed by 10 mM borate/NaOH, 4 M KCl pH 9.1. A suction manifold is used in order to force the fluids through the column. After washing with 3 ml of 10 mM borate/NaOH, 4 KCl pH 9.1 and 0.3 ml 10 mM borate/NaOH pH 9.1, the sample is eluted with 7.5 ml 10 mM borate/NaOH pH 9.1. Without further treatment, eluate is then subjected to CE analysis, following the procedure described above for cyclopiazonic acid. Occasionally a precipitate forms which is removed by centrifugation. The lower limit of sensitivity of the method is approximately 6 ppm.

D. Assay Procedure for Kojic Acid by Thin Layer Chromatography

An aliquot of sample is applied to the opposing sides of TLC plates as described above for CPA and developed using the same solvent systems as for CPA. The dried plates are sprayed with 1% $FeCl_3$ in 0.1 M HCl. The presence of kojic acid in the sample is indicated by a red spot and compared to the intensity of the red spot produced by pure kojic acid applied as a control. The lower limit of detection is 50 ppm.

E. Assay Procedure for 3-NPA by Capillary Electrophoresis

The need for sample purification preparatory to capillary electrophoresis (CE) analysis depends on the conductivity of the sample. If the conductivity is less than 10 mS, the sample is purified by ion exchange over a Varian SAX anion exchanger (Varian Instruments, Palo Alto Calif.) using 0.1 M KCl as the elution buffer. If the conductivity is greater than 100 mS, the sample is extracted using 2-butanol extraction, in which a 2 ml sample is extracted with 6 ml butanol after precipitation with acidification/high salt treatment and redissolving the precipitate in 10 mM Tris/HCl pH 7.0.

HP-CE apparatus, diode array detection, using a capillary of uncoated silica at 50 micro-m and an effective length of 56 cm at a temperature of 30° C. and a conditioning buffer of 25 mM borate/phosphate pH 7.6 are applied. The sample is injected under hydrodynamic pressure over a 20 sec. period. The voltage is set at 30 kV. The lower limit of sensitivity of the method is 6 ppm.

F. Assay Procedure for 3-NPA by Thin Layer Chromatography

Spots of fermentation liquid are applied to TLC plates and developed as described for CPA. They are then sprayed with diazotized p-nitroaniline as described by W. Majak and R. J. Bose, "Chromatographic methods for the isolation of miserotoxin and the detection of aliphatic nitro compounds", Phytochemistry (1974) 13:1005–1010. The intensity and position of the spots relative to the control substance are a measure of the 3-NPA concentrations. Detection level on TLC plates: 25–50 ppm.

Alternatively, 3-NPA is analyzed spectrophotometrically ($\lambda$=540 nm) by adding 50 microliters 1 M NaOH and 70 microliters diazotized p-nitroaniline to 100 microlter sample. Detection level 5–10 ppm.

EXAMPLE 1

A. Construction of a CPA Negative Strain Derived from *A. oryzae* Bz 14

Lyophilized spores of a strain of *Aspergillus oryaze* BZ14 strain were gamma-irradiated at an optimum dose range of between 1000 Gy-1250 Gy, then plated on plates of Screening medium 1 in densities of 25–50 colonies/9 cm plate. Colonies producing cyclopiazonic acid form a red reverse side (the underside of the colony) on Screening 1 medium due to a red insoluble CPA-Fe complex.

Approximately 50,000 colonies from the irradiated spores were screened and 154 CPA deficient colonies, characterized by a creamy/whitish appearance, were isolated. Following re-isolation, 64 strains retained a non-red reverse on plates of Screening medium 1. CPA was not detected in 52 strains by the TLC-plug assay. These strains were then cultured in MDU-1B medium under toxin provoking (5 days at 34° C., 250 rpm) shake flask fermentation conditions. Thirty-six strains presented no detectable levels of CPA in the supernatant as measured by TLC.

B. Construction of a CPA Negative Strain, BECh 1, Derived from *A. oryzae* JaL228

Lyophilized spores of JaL228 were $\gamma$-irradiated and screened as described above. Putative CPA free isolates were grown in shakeflasks on MDU-1B medium under toxin provoking conditions (5 days at 34° C., 250 rpm) and supernatants tested for CPA with the TLC method. The supernatants were tested as they were or as extracts.

For the extraction 50 ml of the whole sample was acidified with 10 ml 0.1 M HCl. This mixture was then vigorously shaken for 3–5 minutes with 70 ml methanol/chloroform (1:2). Following phase separation (approx. 3 hours), the bottom phase (approximately 25 ml) was transferred to a 300 ml beaker and the chloroform allowed to evaporate. The residue was redissolved in 5 ml chloroform, transferred to a 25 ml beaker and the chloroform evaporated. The residue was dissolved in 100 microliters chloroform.

Ten microliters of supernatant or chloroform extract were applied to the opposite edges of 20 cm×20 cm TLC plates and processed as described in the previous chapter on the assays.

Three strains (isolates) including BECh 1 did not produce CPA.

C. Construction of CPA Negative and KA Negative Strains, BECh 2 and BECh 3

BECh 1 was grown on a Cove N slant. Spores were suspended in 0.01% Tween to a density of $3-5 \times 10^6$ and subjected to short-wave UV irradiation (254 nm from germicidal lamp). Spores irradiated with UV doses resulting in 1–5% survival were used in the subsequent screening.

Irradiated spores were diluted in KM2 medium to approx. 0.7 spore/100 microliters, and 100 microliters were inoculated into each well in 96 well microtiter plates. The cultures were incubated statically in a moist chamber at 34° C. for 5–7 days. Then 40 micro-l 1% $FeCl_3$ in 0.1 M HCl was added to each well with signs of growth.

The emergence of a strong red color indicated kojic acid (KA) production; absence of color indicated a colony deficient in kojic acid production.

Alternatively, spores were plated on solidified KM2 (restricted growth with Triton x-100) and when mature colonies were seen the plates were flooded with 1% $FeCl_3$ in 0.1 M HCl. Absence of red zones around colonies indicate putative non-kojic acid producers.

One hundred thirty-two putative KA free colonies, i.e., those giving no colour reaction with $FeCl_3$, were isolated from among approximately 7000 microtiter cultures. However, when tested on the primary KM2 screening agar plates, none of the colonies were confirmed to be KA negative.

Subsequent re-testing in liquid medium under KA provoking conditions of the negative colonies on both solid medium and in static liquid KM2 medium (30°) narrowed the number of KA negative mutants down to 11. When these strains were tested in shake flasks, KA was produced by eight of the strains. The remaining three gave no colour reaction on an assay directly on supernatant nor when checked by TLC. As expected, KA was produced by the control strain BECh 1, when grown in simultaneous parallel cultures. One of the isolated strains exhibited an aberrant morphology. The remaining two isolates were retested for both CPA and KA after prolonged growth on MDU-1B. Neither CPA nor KA was detected. The two strains were named BECh 2 and BECh 3.

D. Construction of a 3-NPA Negative *A. oryzae* Strain which Already is CPA Negative and KA Negative Strain BECh 2 and BECh 3, respectively, are subjected to UV mutagenesis as described above. The irradiated spores are diluted to 0.7 live spore/100 microliters Nakamura medium in 96 well microtiter plates. Incubate for 5–7 days in moist chamber, 30° C.

Fermentation broth samples from wells with growth are either transferred to a new microwell plate and analyzed spectrophotometrically or applied to TLC plates. Strains negative for 3-NPA are recultivated in shakeflasks with Nakamura medium and analyzed for 3-NPA. Strains still negative for 3-NPA are transformed with pCaHj 493 as described in Example 2 and the transformants are treated as described in Example 3.

EXAMPLE 2

Expression of Lipase Gene in *A. oryzae* Strains JAL228 and BECh 1

A. Construction of Plasmid pCaHj493

The lipase plasmid pAHL (WO 97/07202) was digested with BamHI and SalI, and the resulting 916 bp fragment encoding the lipase was isolated.

pCaHj 483, as described in WO 98/00529, was digested with BamHI and XhoI, and the 6757 bp vector fragment was ligated to the lipase fragment. The ligation mixture was used to transform *E. coli* DH 5α cells, and a transformant harboring the expected plasmid was isolated. The plasmid was termed pCaHj 493.

B. Transformation of pCaHj 493 into JaL228 and BECh-1

*Aspergillus oryzae* strains JaL228 and BECh1 were transformed with pCaHj493 using selection on acetamide as described in EP-A-0531372. Transformants were spore reisolated twice. Spores from a second reisolation of each transformant were tested for lipase production in shake flasks and microtiter dish cultures.

EXAMPLE 3

A. Lipase Production in a CPA Negative and a CPA Positive *A. oryzae* Strain

Eighteen JaL228 transformants and 30 BECh 1 transformants, prepared as described in Example 2, were tested for the production of lipase in shake flask cultures.

Cove N slants of the transformants were harvested using 10 ml of a 0.1% Tween solution, and the spore suspension was used as the inoculum in 100 ml of G1-Gly medium in 500 ml two-baffled shake flasks. The cultures were incubated on a rotary shaker at 250 rpm, 34° C. for 24 hours. Then 10 ml of the G1-Gly culture was transferred to 100 ml 1/5MDU-2BP in 500 ml shake flasks and incubated further at 34° C., 250 rpm.

Samples were taken after 50 hours, filtered through Miracloth and centrifuged (4000×g). Lipase concentrations (expressed in LU/ml) in the supernants were detected using the Single radial immunodiffusion method (Scand. J. Immunol. Vol. 17, suppl. 10, 41–56, (1983), "Handbook of Immunoprecipitation-in-Gel Techniques", N. H. Axelsen, ed., Blackwell Scientific Publications, 1983).

The 30 CPA negative BECh 1 transformants had lipase yields as high as or better than the 18 JaL228 CPA positive transformants. Table 2 below gives an overview of the distributions.

B. Xylanase Production by CPA Negative and CPA Positive *A. oryzae* Strains

Ten strains (prepared in Example 1A) with no detectable CPA production and three strains in which CPA was detectable were evaluated for production of xylanase. The results are summarized in Table 1 below. Column 2 shows the amount of xylanase, measured in fungal xylanase units (FXU) as assayed by the Single radial immunodiffusion method (Scand. J. Immunol. Vol 17, suppl. 10, 41–56, 1983, Handbook of Immunoprecipitation-in-Gel Techniques, N. H. Axelsen, ed., Blackwell Scientific Publications, produced in shake flask cultures.

The results show that the CPA negative strains can produce xylanase in amounts comparable to CPA positive strains.

TABLE 1

| Strain | FXU | CPA/ppm |
| --- | --- | --- |
| 2–5 | 360 | <2 |
| 3–34 | 440 | <2 |
| 4–2 | 550 | <2 |
| 5–1 | 250 | <2 |
| 5–2 | 475 | <2 |
| 7–1 | 530 | <2 |
| 7–2 | 475 | <2 |
| 9–5 | 370 | <2 |
| 10–4 | 300 | <2 |
| 12–2 | 365 | <2 |
| 1–1 | 600 | 2–3 |
| 1–3 | 650 | 20 |
| 3–1 | 635 | 7 |

<2 = below detection limit

C. Lipase Production in CPA Negative and KA Negative Strains

The two CPA and KA free *A. oryzae* strains BECh 2 and BECh 3 were transformed with the plasmid pCaHj 493 as described in Example 2. Transformants were spore isolated twice. Spores from the second re-isolation of each transformant were tested for lipase production as described in Example 2.

Table 2 shows the frequency distributions of the lipase yields of transformants from these two strains. The results show that no deterioration in expression potential occurred as compared to the values given for the *A. oryzae* strains BECh 1 and JaL228.

From the same spore suspension used for the lipase production cultures, MDU1B shakeflasks for CPA production were inoculated and incubated for 5 days as described previously. DPA analysis was done according to section 5B2. None of the BECh1 strains produced CPA whereas 17 of the 18 JaL228 strains gave more than 25 ppm, the majority more than 100 ppm CPA.

TABLE 2

| Strain | N | Median LU/ml | Mean LU/ml | Minimum LU/ml | Maximum LU/ml | Std. Dev. LU/ml |
| --- | --- | --- | --- | --- | --- | --- |
| BECh2 | 50 | 3101 | 3203 | 350 | 6329 | 1490 |
| BECh3 | 47 | 2619 | 2662 | 203 | 5455 | 1057 |
| JaL228 | 18 | 1890 | 2330 | 635 | 4664 | 1361 |
| BECh1 | 30 | 3025 | 2733 | 876 | 4097 | 879 |

EXAMPLE 4

Identification and Genomic Cloning of the *A. oryzae* DCAT-S Gene

A. Identification of the *A. oryzae* Dimethylallyl-cycloacetoacetyl-L-tryptophan Synthase (DCAT-S) Gene The cDNA clone (pJaL499) harbors the DNA sequence shown in SEQ ID NO: 1, which has been identified to be involved in the CPA biosynthesis by its homology to a dimethylallyltryptophan synthase (DMAT-S) from *Claviceps purpurea*. Sequencing of the *A. oryzae* cDNA clone showed that it was 1393 base pairs in length (SEQ. ID. NO: 1) and encoded an 473 amino acid polypeptide (SEQ. ID. NO: 2) that was 42.1% identical to the DMAT-S from *Claviceps purpurea*.

The *A. oryzae* DCAT-S polypeptide is involved in the synthesis of beta-CPA from cyclo-acetoacetyl-L-tryptophan and dimethylallylpyrophosphate, Nethling D. C. and R. M. McGrath, Can. J. Microbiol. (1977) 23:856–872.

Chromosomal DNA from strains JaL228 and BECh 1 was prepared. The DNA was digested with BglII, NcoI, XhoI and SpeI and analyzed by Southern blotting, using the 1 kb $^{32}$P-labelled BglII DNA fragment from pJaL499 containing the DCAT-S gene as a probe. Southern blot analysis showed that the CPA producing strain JaL228 has one DCAT-S gene, whereas in BECh 1 the DCAT-S gene had been deleted from the chromosome.

B. Cloning of a Genomic Clone of the DCAT-S Gene

Figure 1:
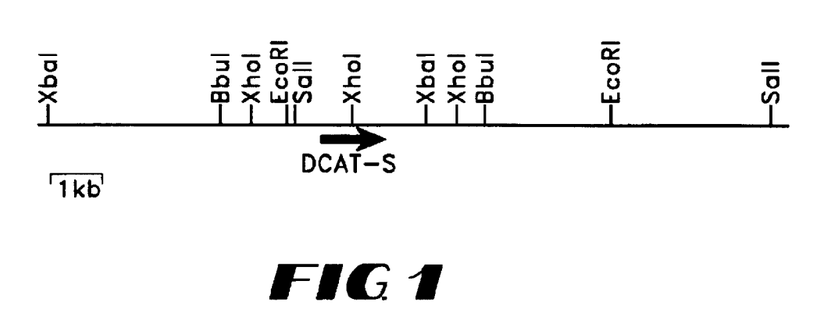
FIG. 1 shows the genomic restriction mapping of the *Aspergillus oryzae* DCAT-S gene carried out with the restriction enzymes EcoRI, SalI, BbuI, XhoI and XbaI, using the 1 kb $^{32}$P-labelled DNA BglII fragment from pJaL499 containing the DCAT-S gene as a probe.

Genomic restriction mapping of the *A. oryzae* DCAT-S gene is carried out with the following restriction enzymes: EcoRI, SalI, BbuI, XhoI, and XbaI, using the 1 kb $^{32}$P-labelled DNA BglII fragment from pJaL499 containing the DCAT-S gene as a probe (FIG. 1). This shows that there is only one copy of the DCAT-S gene.

Genomic DNA of JaL228 is partially digested with either Tsp509I or run on a 0.7% agarose gel. Fragments with a size between 7 and 10 kb are purified.

The purified DNA is then cloned into Lambda ZAP II using protocols provided by the manufacturer (Stragtagene®). In vivo excision and recircularisation of any clone insert contained within the lambda vector to form a phagemid containing the cloned insert is done for the DNA libraries, according to instructions provided by the manufacturer. Screening for clones encoding the DCAT-S gene is performed by colony hybridization using the 1 kb $^{32}$P-labelled DNA BglII fragment from pJaL499 containing the DCAT-S gene as a probe, as outlined in standard methodology textbooks (e.g., J. Sambrook, E. F. Fritsch, and T. Maniatis, eds. (1989) "Molecular Cloning: A Laboratory Manual", Second Ed., Cold Spring Harbor Laboratory Press, Cold Spring Harbor, N.Y.).

EXAMPLE 5

Generation of an *Aspergillus oryaze* CPA Negative Strain by Genomic Disruption of the *Aspergillus oryaze* Dimethylallyl-cycloacetoacetyl-L-tryptophan Synthase (DCAT-S)

The DCAT-S gene is disrupted by the one-step gene replacement method (B. L. Miller et al., Mol. Cell. Biol. (1985) 5:1714–1721, and G. May, in Applied Molecular Genetics of Filamentous Fungi, pp. 1–25; J. R. Kinghorn and G. Turner, eds.; Blakie Academic and Professional, 1992) in a pyrG minus strain of *A. oryzae*, using the *A. oryzae* pyrG gene as a selection marker.

A. Construction of the DCAT-S Disruption Plasmid

Plasmid pJaL499 is digested with SacII and treated with Klenow polymerase to create blunt ends, and with bacterial alkaline phosphatase according to instructions of the manufacturer (Boehringer Mannheim) to remove the 5' phosphate groups, and then phenol extracted and precipitated.

Figure 2:
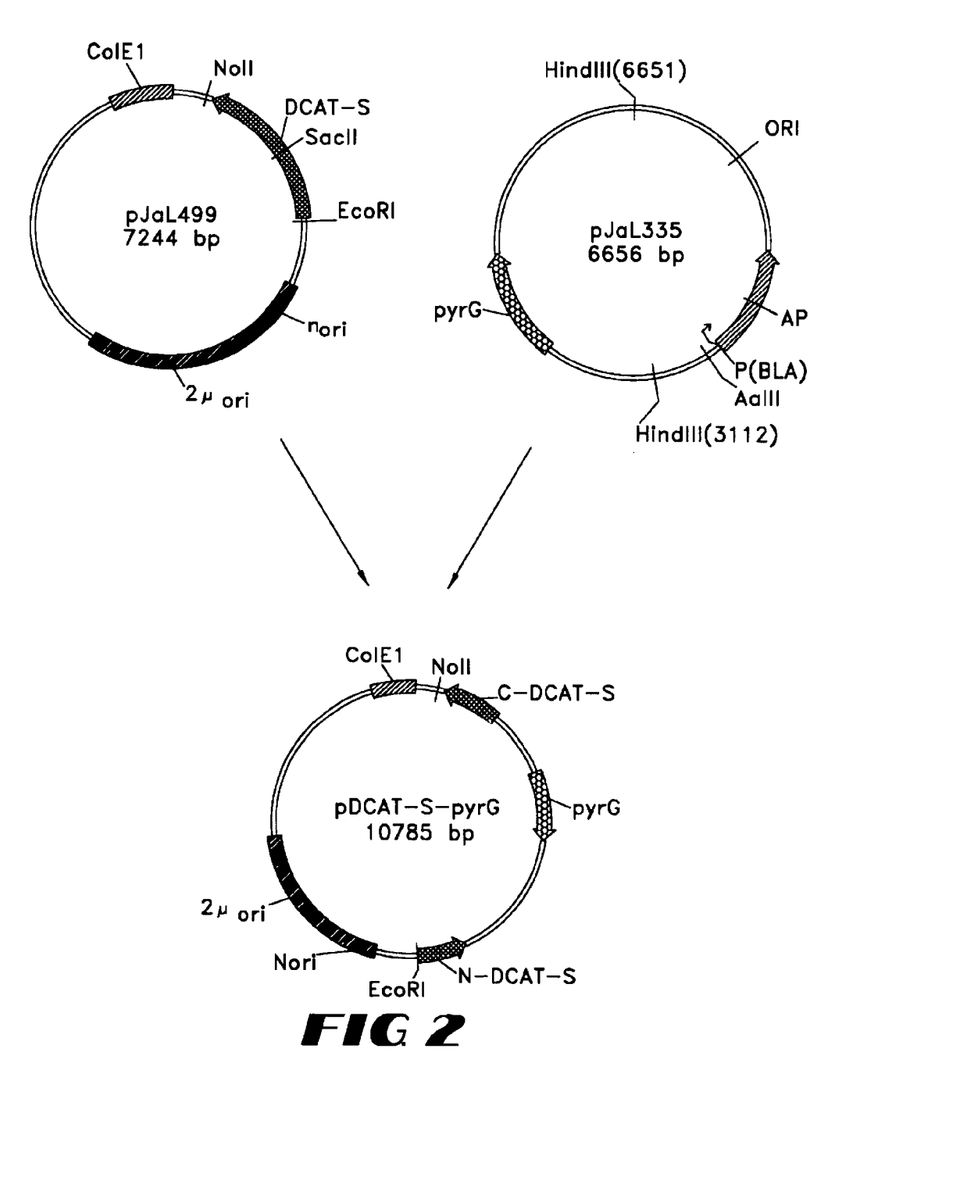
FIG. 2 shows the construction of the disruption plasmid p(DCAT-S-pyrG).

Plasmid pJaL335, described in WO 98/12300, is digested with HindIII to obtain a 3.5 kb fragment comprising the *A. oryzae* pyrG gene, treated with Klenow polymerase to create blunt ends, isolated by gel electrophoresis, and purified. The two fragments were then mixed together and ligated. After transformation into *E. coli*, the colonies carrying the correct plasmid were identified by restriction enzyme digestion of mini-plasmid preparations. The construction of the disruption plasmid (pDCAT-S-pyrG) is summarized in FIG. 2.

B. Isolation of a pyrG Minus *A. oryzae* Strain, JaL250

The *A. oryzae* strain JaL228 is screened for resistance to 5-fluoro-orotic acid to identify spontaneous pyrG mutants. One strain, named JaL250, is identified as being pyrG minus. The mutant is uridine dependent, therefore it can be transformed with the wild type pyrG gene and transformants are selected by the ability to grow in the absence of uridine.

C. Construction of an *Aspergillus oryaze* DCAT-S Minus Strain

The 4.9 kb NotI-EcoRI fragment of the plasmid pDCAT-S-pyrG is gel purified and used to transform the *A. oryzae* strain JaL250 as described by Christensen et al., Biotechnology (1988) 6:1419–1422. Transformants are then selected by their ability to grow in the absence of uridine. After reisolation twice the transformants are screened for their ability to produce CPA, as described in Example 1.

In order to confirm that the DCAT-S gene is disrupted chromosomal DNA is prepared from transformants that do not produce CPA. The DNA is digested with EcoRI and analyzed by Southern blotting, using the 1 kb $^{32}$P labelled DNA BglII fragment from pJaL499 containing the DCAT-S gene as a probe. Transformants that carry a disruption of the DCAT-S gene are recognized by the shift of the wild type EcoRI band on 6.3 kb to a EcoRI band on 9.8 kb.

EXAMPLE 6
Confirmation that BECh1 and BECh2 Lack Two Genes from the Aflatoxin Biosynthetic Pathway Cluster The presence of the aflR and omtA aflatoxin genes from the aflatoxin biosynthetic pathway cluster in *A. oryzae* IFO4177 and a number of derivatives thereof have been looked for. The aflR homologue from *A. oryzae* IFO4177 was isolated by PCR from genomic DNA with the primers 5956 (5'-GGATCCAGGGCTCCCTGGAG-3') (SEQ ID NO: 3) and 5955 (5'-CCTGACCAGCCAGATCTCCT-3') (SEQ ID NO: 4). A 0.9 kb PCR fragment was obtained and cloned into the vector pCR2 from Invitrogen. The identity of the cloned fragment was confirmed by sequencing the resulting plasmid, pToC280, with the M13 forward (–40) and reverse primers. The omtA homologue was also isolated from genomic IFO4177 DNA by PCR with the primers 6120 (5'-AGTGAGAGAACTCCCTCCTC-3') (SEQ ID NO: 5) and 6121 (5'-CCATATCTTCTCAGTCTCCA-3') (SEQ ID NO: 6). A 1.2 kb fragment was obtained and cloned into the vector pCR2 from Invitrogen and the resulting plasmid, pToC276, was sequenced with the M13 forward (–40) and reverse primers to confirm the identity of the cloned fragment.

The cloned fragments of aflR and omtA were used as 32P-labelled probes in a hybridization experiment. Genomic DNA from IFO4177, JaL228, BECh1 and BECh2 were digested with the restriction enzyme ecoRI and the generated fragments were separated on a 0.7% agarose gel. The DNA was blotted onto a membrane and hybridized under stringent conditions with the two 32P labelled probes one at a time (methods are described in J. Sambrook, E. F. Fritsch, T. Maniatis, eds (1989) "Molecular Cloning: A Laboratory Manual", Second ed., Cold Spring Harbor Laboratory Press, Cold Spring Harbor, N.Y.). The blot showed positive hybridization signals with both probes from IFO4177 and JaL228, while no bands were visible in the lanes containing BECh1 and BECh2 DNA. In the IFO4177 and JaL228 lanes an approximately 3.8 kb fragment could be seen with the omtA probe and two band of approximately 0.5 and 4.3 kb could be seen with the aflR probe.

Consequently, *A. oryzae* IFO4177 contains at least two genes from the aflatoxin biosynthetic pathway, namely the aflR and the omtA genes. In *A. flavus* and *A. parasiticus* the two genes are separated by approximately 32 kb (Woloshuk, C. P. and Prieto, R, FEMS Microbiology Letter (1998) 160:169–176). None of these genes are present in the IFO4177 derivatives BECh1 and BECh 2.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated dimethylallyl-cycloacetoacetyl-L-tryptophan synthase, which is encoded by a nucleotide sequence which hybridizes with SEQ ID NO: 1 under medium stringency conditions, wherein the medium stringency conditions are defined by prehybuidization and hybridization at 42° C. in 5×SPPE, 0.3% SDS, 200 micrograms/ml sheared and denatured salmon sperm DNA, and 35% formamide, followed by washing three times for 30 minutes with 2×SSC and 0.2% SDS at 65° C.

2. An isolated dimethylallyl-cycloacetoacetyl-L-tryptophun synthase which is encoded by a nucleotide sequence which hybridizes with SEQ ID NO: 1 under high stringency conditions, wherein the high stringency conditions are defined by prehybridization and hybridization at 42° C. in 5×SPPE, 0.3% SDS, 200 micrograms/ml sheared and denatured salmon sperm DNA, and 50% formamide, followed by washing three times for 30 minutes with 2×SSC and 0.2% SDS at 70° C.

3. An isolated dimethylallyl-cycloacetoacetyl-L-tryptophan synthase, which is encoded by a nucleotide sequence which hybridizes with SEQ ID NO: 1 under high stringency conditions, wherein the high stringency conditions are defined by prehybridization and hybridization at 42° C. in 5×SPPE, 0.3% SDS, 200 micrograms/ml sheared and denatured salmon sperm DNA, and 50% formamide, followed by washing three times for 30 minutes with 2×SSC and 0.2% SDS at 75° C.

4. The dimethylallyl-cycloaoetoacetyl-L-tryptophan synthase of claim 1, which is obtained from an *Aspergillus* strain.

5. The dimethylallyl-cycloacetoacetyl-L-tryptophan synthase of claim 4, which is obtained from an *Aspergillus oryzae* strain.

6. The dimethylallyl-cycloacetoacetyl-L-tryptophan synthase of claim 2, which is obtained from an *Aspergillus* strain.

7. The dimethylallyl-cycloacetoacetyl-L-tryptophan synthase of claim 6, which is obtained from an *Aapergillus oryzee* strain.

8. The dimethylallyl-cycloacetoacetyl-L-tryptophan synthase of claim 3, which is obtained from an *Aspergillus* strain.

9. The dimethylallyl-cycloacetoacetyl-L-tryptophan synthase of claim 8, which is obtained from an *Aspergillus oryzee* strain.

10. An isolated dimethylallyl-cycloacetoacetyl-L-tryptophan synthase which comprises an amino acid sequence of SEQ ID NO: 2 or a fragment thereof which has dimethylallyl-cycloacetoacetyl-L-tryptophan synthase activity.

11. The dimethylallyl-cycloacetoacetyl-L-tryptophan synthase of claim 10, which comprises an amino acid sequence of SEQ ID NO: 2.

12. The dimethylallyl-cycloacetoacetyl-L-tryptophan synthase of claim 10, which consists of an amino acid sequence of SEQ ID NO: 2.

* * * * *

SEQUENCE LISTING

<160> NUMBER OF SEQ ID NOS: 6

<210> SEQ ID NO 1
<211> LENGTH: 1393
<212> TYPE: DNA
<213> ORGANISM: Artificial Sequence
<220> FEATURE:
<223> OTHER INFORMATION: Primer 5956
<221> NAME/KEY: CDS
<222> LOCATION: (15)...(1328)

<400> SEQUENCE: 1

```
ccgaaagctg agca atg gag atc tcc aag aaa gca gca aca ctg ctg cca         50
              Met Glu Ile Ser Lys Lys Ala Ala Thr Leu Leu Pro
               1               5                  10 aag ccc ttc tac gtg ctg agt caa gcc ctg aac ctc tcg aac aag gac         98
Lys Pro Phe Tyr Val Leu Ser Gln Ala Leu Asn Leu Ser Asn Lys Asp
         15                  20                  25 cac aca aaa tgg tgg tat agc aca gct ccg atg ttt gcc acc atg atg        146
His Thr Lys Trp Trp Tyr Ser Thr Ala Pro Met Phe Ala Thr Met Met
     30                  35                  40 gcg ggg gcc ggc tat gat gtt cac gca cag tac aag ttc ctc tgt atc        194
Ala Gly Ala Gly Tyr Asp Val His Ala Gln Tyr Lys Phe Leu Cys Ile
 45                  50                  55                  60 cac cgt gag gtc atc atc ccg gcg ttg ggt cca tac cca gaa aag ggt        242
His Arg Glu Val Ile Ile Pro Ala Leu Gly Pro Tyr Pro Glu Lys Gly
                 65                  70                  75 cag ccc atg cac tgg aag agt cat ctc aca cgc ttc gga ctt cct ttc        290
Gln Pro Met His Trp Lys Ser His Leu Thr Arg Phe Gly Leu Pro Phe
             80                  85                  90
```

```
gag ctg agc ttc aat tac tcc aaa tca cta cta cgg ttt gca ttc gag      338
Glu Leu Ser Phe Asn Tyr Ser Lys Ser Leu Leu Arg Phe Ala Phe Glu
         95                 100                 105 ccc ctc ggt tcc ctg acg gga acg aag gat gat cca ttc aac acc cag      386
Pro Leu Gly Ser Leu Thr Gly Thr Lys Asp Asp Pro Phe Asn Thr Gln
    110                 115                 120 gca atc agg cct gtt ctc cag gac ctc aag gcc atg gtt cca ggg ctt      434
Ala Ile Arg Pro Val Leu Gln Asp Leu Lys Ala Met Val Pro Gly Leu
125                 130                 135                 140 gac ctg gaa tgg ttc gat cat ttc act aaa gca ttg gtc gtt tcg gag      482
Asp Leu Glu Trp Phe Asp His Phe Thr Lys Ala Leu Val Val Ser Glu
                145                 150                 155 gaa gag gct cgg act ctg cta gat cga gat att gag atc ccc gtc ttc      530
Glu Glu Ala Arg Thr Leu Leu Asp Arg Asp Ile Glu Ile Pro Val Phe
            160                 165                 170 aag aca cag aac aaa ctg gca gcc gat ctg gag cca tct ggc gat att      578
Lys Thr Gln Asn Lys Leu Ala Ala Asp Leu Glu Pro Ser Gly Asp Ile
        175                 180                 185 gtc ttg aag acc tac atc tac ccg cgg atc aag tcg atc gcg acc ggg      626
Val Leu Lys Thr Tyr Ile Tyr Pro Arg Ile Lys Ser Ile Ala Thr Gly
    190                 195                 200 acc cca aaa gag aga ctc atg ttt gac gca atc aag gct gcc gac aag      674
Thr Pro Lys Glu Arg Leu Met Phe Asp Ala Ile Lys Ala Ala Asp Lys
205                 210                 215                 220 ttt ggc aaa gtt gcc act cca ctg gca atc ctc gag gag ttt ata gct      722
Phe Gly Lys Val Ala Thr Pro Leu Ala Ile Leu Glu Glu Phe Ile Ala
                225                 230                 235 gag cga gca ccc acc ctc ctc ggc cac ttt ctc tca tgc gat ttg gtc      770
Glu Arg Ala Pro Thr Leu Leu Gly His Phe Leu Ser Cys Asp Leu Val
            240                 245                 250 aag ccg tcc gag tcc cga atc aag gtc tac tgt atg gaa cgc cag ctc      818
Lys Pro Ser Glu Ser Arg Ile Lys Val Tyr Cys Met Glu Arg Gln Leu
        255                 260                 265 gac ctg gcc tcc atc gaa ggt att tgg act ctc aac ggg cga cgg aac      866
Asp Leu Ala Ser Ile Glu Gly Ile Trp Thr Leu Asn Gly Arg Arg Asn
270                 275                 280 gat cca gag aca ctg gat ggt ctg gat gcg ctg agg gag ctg tgg cag      914
Asp Pro Glu Thr Leu Asp Gly Leu Asp Ala Leu Arg Glu Leu Trp Gln
285                 290                 295                 300 cta ttg ccc gtc acg gag ggt ctg tgt cca ctg ccg aac tgc ttt tac      962
Leu Leu Pro Val Thr Glu Gly Leu Cys Pro Leu Pro Asn Cys Phe Tyr
                305                 310                 315 gag ccg ggt acc tca ccg cag gag cag ctc ccc ttc att ata aat ttt      1010
Glu Pro Gly Thr Ser Pro Gln Glu Gln Leu Pro Phe Ile Ile Asn Phe
            320                 325                 330 acc ttg tct cct aaa agc gca ctt ccc gaa cca cag atc tat ttc cct      1058
Thr Leu Ser Pro Lys Ser Ala Leu Pro Glu Pro Gln Ile Tyr Phe Pro
        335                 340                 345 gct ttt ggg cag aac gac aaa acc atc gcg gaa gga ttg gcc acc ttc      1106
Ala Phe Gly Gln Asn Asp Lys Thr Ile Ala Glu Gly Leu Ala Thr Phe
    350                 355                 360 ttt gag agc aga ggt tgg ggt ggc ttg gct aag agc tat cca gcg gat      1154
Phe Glu Ser Arg Gly Trp Gly Gly Leu Ala Lys Ser Tyr Pro Ala Asp
365                 370                 375                 380 ttg gca tcc tac tat ccc gat gtg gac ctg cag acc gca aat cac ctg      1202
Leu Ala Ser Tyr Tyr Pro Asp Val Asp Leu Gln Thr Ala Asn His Leu
                385                 390                 395 cag gcg tgg atc tcc ttc tct tac aag ggg aaa aaa ccg tac atg agt      1250
Gln Ala Trp Ile Ser Phe Ser Tyr Lys Gly Lys Lys Pro Tyr Met Ser
            400                 405                 410
```

```
gtg tac ctc cat acc ttc gaa gcg ttc agt gct gct gcc cag gag gtg        1298
Val Tyr Leu His Thr Phe Glu Ala Phe Ser Ala Ala Ala Gln Glu Val
            415                 420                 425 gct atg tgt cac gat ggc cac aat cct tag gactagttta tcccttcatt          1348
Ala Met Cys His Asp Gly His Asn Pro *
    430                 435 ctatgcatcc gttgaatgtg ttggtcgaaa aaaaaaaaaa aaaaa                      1393
```

<210> SEQ ID NO 2
<211> LENGTH: 437
<212> TYPE: PRT
<213> ORGANISM: Artificial Sequence
<220> FEATURE:
<223> OTHER INFORMATION: Primer 5956

<400> SEQUENCE: 2

```
Met Glu Ile Ser Lys Lys Ala Ala Thr Leu Leu Pro Lys Pro Phe Tyr
  1               5                  10                  15

Val Leu Ser Gln Ala Leu Asn Leu Ser Asn Lys Asp His Thr Lys Trp
                 20                  25                  30

Trp Tyr Ser Thr Ala Pro Met Phe Ala Thr Met Met Ala Gly Ala Gly
             35                  40                  45

Tyr Asp Val His Ala Gln Tyr Lys Phe Leu Cys Ile His Arg Glu Val
 50                  55                  60

Ile Ile Pro Ala Leu Gly Pro Tyr Pro Glu Lys Gly Gln Pro Met His
 65                  70                  75                  80

Trp Lys Ser His Leu Thr Arg Phe Gly Leu Pro Phe Glu Leu Ser Phe
                 85                  90                  95

Asn Tyr Ser Lys Ser Leu Leu Arg Phe Ala Phe Glu Pro Leu Gly Ser
                100                 105                 110

Leu Thr Gly Thr Lys Asp Asp Pro Phe Asn Thr Gln Ala Ile Arg Pro
            115                 120                 125

Val Leu Gln Asp Leu Lys Ala Met Val Pro Gly Leu Asp Leu Glu Trp
130                 135                 140

Phe Asp His Phe Thr Lys Ala Leu Val Val Ser Glu Glu Glu Ala Arg
145                 150                 155                 160

Thr Leu Leu Asp Arg Asp Ile Glu Ile Pro Val Phe Lys Thr Gln Asn
                165                 170                 175

Lys Leu Ala Ala Asp Leu Glu Pro Ser Gly Asp Ile Val Leu Lys Thr
            180                 185                 190

Tyr Ile Tyr Pro Arg Ile Lys Ser Ile Ala Thr Gly Thr Pro Lys Glu
        195                 200                 205

Arg Leu Met Phe Asp Ala Ile Lys Ala Asp Lys Phe Gly Lys Val
    210                 215                 220

Ala Thr Pro Leu Ala Ile Leu Glu Glu Phe Ile Ala Glu Arg Ala Pro
225                 230                 235                 240

Thr Leu Leu Gly His Phe Leu Ser Cys Asp Leu Val Lys Pro Ser Glu
                245                 250                 255

Ser Arg Ile Lys Val Tyr Cys Met Glu Arg Gln Leu Asp Leu Ala Ser
            260                 265                 270

Ile Glu Gly Ile Trp Thr Leu Asn Gly Arg Arg Asn Asp Pro Glu Thr
        275                 280                 285

Leu Asp Gly Leu Asp Ala Leu Arg Glu Leu Trp Gln Leu Leu Pro Val
    290                 295                 300

Thr Glu Gly Leu Cys Pro Leu Pro Asn Cys Phe Tyr Glu Pro Gly Thr
```

```
               305                 310                 315                 320
Ser Pro Gln Glu Gln Leu Pro Phe Ile Ile Asn Phe Thr Leu Ser Pro
                325                 330                 335

Lys Ser Ala Leu Pro Glu Pro Gln Ile Tyr Phe Pro Ala Phe Gly Gln
                340                 345                 350

Asn Asp Lys Thr Ile Ala Glu Gly Leu Ala Thr Phe Phe Glu Ser Arg
                355                 360                 365

Gly Trp Gly Gly Leu Ala Lys Ser Tyr Pro Ala Asp Leu Ala Ser Tyr
                370                 375                 380

Tyr Pro Asp Val Asp Leu Gln Thr Ala Asn His Leu Gln Ala Trp Ile
385                 390                 395                 400

Ser Phe Ser Tyr Lys Gly Lys Lys Pro Tyr Met Ser Val Tyr Leu His
                405                 410                 415

Thr Phe Glu Ala Phe Ser Ala Ala Ala Gln Glu Val Ala Met Cys His
                420                 425                 430

Asp Gly His Asn Pro
                435

<210> SEQ ID NO 3
<211> LENGTH: 20
<212> TYPE: DNA
<213> ORGANISM: Artificial Sequence
<220> FEATURE:
<223> OTHER INFORMATION: Primer 5956

<400> SEQUENCE: 3
ggatccaggg ctccctggag                                                  20

<210> SEQ ID NO 4
<211> LENGTH: 20
<212> TYPE: DNA
<213> ORGANISM: Artificial Sequence
<220> FEATURE:
<223> OTHER INFORMATION: Primer 5955

<400> SEQUENCE: 4
cctgaccagc cagatctcct                                                  20

<210> SEQ ID NO 5
<211> LENGTH: 20
<212> TYPE: DNA
<213> ORGANISM: Artificial Sequence
<220> FEATURE:
<223> OTHER INFORMATION: Primer 6120

<400> SEQUENCE: 5
agtgagagaa ctccctcctc                                                  20

<210> SEQ ID NO 6
<211> LENGTH: 20
<212> TYPE: DNA
<213> ORGANISM: Artificial Sequence
<220> FEATURE:
<223> OTHER INFORMATION: Primer 6121

<400> SEQUENCE: 6
ccatatcttc tcagtctcca                                                  20
```